United States Patent
Plank et al.

(10) Patent No.: US 8,072,588 B2
(45) Date of Patent: *Dec. 6, 2011

(54) DENTAL LIGHT CURING DEVICE COUPLED TO A LIGHT MEASURING DEVICE

(75) Inventors: Wolfgang Plank, Rankweil (AT); Bruno Senn, Buchs (CH)

(73) Assignee: Ivoclar Vivadent AG, Schaan (LI)

( * ) Notice: Subject to any disclaimer, the term of this patent is extended or adjusted under 35 U.S.C. 154(b) by 241 days.

This patent is subject to a terminal disclaimer.

(21) Appl. No.: 12/288,581

(22) Filed: Oct. 22, 2008

(65) Prior Publication Data

US 2009/0114844 A1 May 7, 2009

(30) Foreign Application Priority Data

Nov. 5, 2007 (DE) .......................... 10 2007 052 643

(51) Int. Cl.
*G01J 1/42* (2006.01)

(52) U.S. Cl. ......................................... 356/218; 356/51

(58) Field of Classification Search .................. 356/364; 433/29, 215; 250/372

See application file for complete search history.

(56) References Cited

U.S. PATENT DOCUMENTS

| | | | |
|---|---|---|---|
| 5,115,126 A | 5/1992 | Ams | |
| 6,485,301 B1 * | 11/2002 | Gemunder et al. | 433/29 |
| 7,267,546 B2 * | 9/2007 | Scott et al. | 433/29 |
| 2006/0139722 A1 * | 6/2006 | Kayser et al. | 359/246 |
| 2008/0023625 A1 | 1/2008 | Plank | |

* cited by examiner

*Primary Examiner* — Tarifur Chowdhury
*Assistant Examiner* — Tara S Pajoohi
(74) *Attorney, Agent, or Firm* — Ann M. Knab

(57) ABSTRACT

The invention relates to a light measuring device 34, in particular for dental light curing devices, for detecting the illumination intensity of a light source 19, which is arranged, in particular, in the light curing device, to which a light guiding device, in particular, having a light exit surface 21 at its outlet, is connected, the light measuring device 34 having at least four measurement fields 38 distributed in two dimensions.

21 Claims, 2 Drawing Sheets

DENTAL LIGHT CURING DEVICE COUPLED TO A LIGHT MEASURING DEVICE

CROSS-REFERENCE TO RELATED APPLICATIONS

This application claims foreign priority benefits under 35 U.S.C. §119(a)-(d) from German patent application ser. no. P 10 2007 052 643.3 filed Nov. 5, 2007.

TECHNICAL FIELD

The invention relates to a light measuring device, in particular for dental light curing devices, and more particularly to such a device which detects the illuminating intensity of a light that exits from the light exit surface of a light guiding device of the light curing device.

BACKGROUND OF THE INVENTION

A light measuring device of the type mentioned above is disclosed, for example, in U.S. Pat. No. 5,115,126. In the case of this light measuring device, which is used for testing endoscopes, the light emitted from a light source is fed via a light guiding device to a sensor arrangement, the endoscope there being tested by comparing the output signal of sensors.

It has already been proposed once to implement a sensor that has a smaller diameter than the light guide and its light exit surface. This solution attempts to enable measurement of the output illumination intensity independently of the diameter of the light exit surface. However, with this solution there is the grave disadvantage that fundamentally only the luminous density in the measured region of the light exit surface is detected. This means that only a lesser fraction in percentage terms of the emitted light power is detected in conjunction with a comparatively large light exit surface, and so erroneous measurements occur to this extent on different sizes of the light exit surfaces.

In particular, even in the case of this solution it is not possible to conduct a distance measurement in which the light curing device is thus merely held over the sensor field in order to determine whether the emitted illumination intensity is still sufficient, because erroneous measurements then always occur in the case of this solution owing to the beam expansion.

In accordance with published patent application US 2008-0023625-A1, it has been proposed to use a one-dimensional arrangement of light sensors, and their output signal in order to determine the light power of a light source. This solution is simple in principle and constitutes an improvement against the previously known solutions. On the other hand, this design is not able to deliver an exact measurement result when the light exit surface has a shape deviating from the circular one.

By contrast, it is the object of the invention to provide a light measuring device that enables a reliable and simple determination of the illumination intensity independently of the shape of a light exit surface.

OBJECTS AND SUMMARY OF THE INVENTION

It is provided according to the invention that the measurement fields provided for the light measuring device are distributed in at least two dimensions. In a Cartesian coordinate system, the measurement fields can be distributed in the X- and Y-directions, for example, it also being possible, however, to utilize a third dimension by arranging measurement fields in the Z-direction, that is to say one below another, or to use a coordinate system other than the Cartesian one.

Surprisingly, this inventive measure can be used, preferably in combination with the measure of configuring the matrix defined by the measurement fields to be greater than the light exit surface in order to detect the illumination intensity of the light source in a surprisingly simple way by integrating the output signals of the measurement fields. To this end, the surroundings of the measurement fields—apart from the light source—are preferably darkened such that measurement fields to which the light source have not been applied emit an output signal of magnitude zero. By contrast, scattered light, which is emitted outside the focal region, the "illuminating spot" of the light source, is detected by the surrounding measurement fields and, to this extent, incorporated into the assessment of the integrated illumination intensity.

However, the light measuring device preferably has a stop that can also be replaced by a corresponding mark and is intended to serve as a reference mark for the light measurement, specifically in that the light exit surface is mounted on the measurement field arrangement. The advantage of this solution is the distinct reduction of scattered light such that the integrated measured illumination intensity of the measurement fields corresponds to the actual light emission, for example of the dental light curing device.

Owing to the two-dimensional or at least two-dimensional detection of the illumination intensity, the detection is independent in principle of the form of the light source. Whereas optical fiber rods typically emit a circular light spot, there are more and more dental light curing devices on offer in which a chip arrangement at the tip of a guide rod effects the light emission, and even when a positive lens is mounted the light is then typically not emitted in a circular fashion, but a rectangular one with rounded corners. Owing to the inventive arrangement of measurement fields, it is possible nevertheless to avoid measurement fields, specifically even when the light curing device is mounted obliquely or in a twisted fashion on the measurement field arrangement.

Surprisingly, it is also possible to compensate obliquity errors: the effect of the obliquity is that the measurement fields with an acute impingement angle are typically illuminated more strongly, and the measurement fields with an obtuse impingement angle are typically illuminated more weakly. The summed measurement of the measurement fields on which light has impinged determines in turn, by contrast, substantially the same measurement result.

In an advantageous refinement of the invention, it is possible for the obliquity error thus detected to be additionally compensated by a control device that undertakes an exact correction in the manner of a correction table in the event of different illumination intensities of the measurement fields that correspond to a gradient and, to this extent, indicate the obliquity of the light curing device.

According to the invention, it is also particularly advantageous that measurement fields arranged in the manner of a matrix are available inexpensively. For example, CCD sensors can be used that offer a multiplicity of measurement fields, such as, for example, 512×512 measurement fields, or even 1024×1024 measurement fields, and thus enable even light spot boundaries to be exactly evaluated with sensitivity.

Such sensors can also be used as an evaluation unit, the detected measurement signals being, for example, buffered in shift registers and being retrieved cyclically by an evaluation device. Such a sensor has a measurement field surface of, for example 25×25 mm that consequently is substantially larger than the diameter or the side length of the light exit surface of the light curing device, which can amount to 3 mm or 5 mm, for example.

Consequently, it is particularly advantageous according to the invention that the detection and calibration of the light curing device is possible even without exact alignment on the measurement surface.

In a further preferred refinement, it is provided that the measurement fields extend in two mutually perpendicular dimensions in a prescribed grid size and have a spectral sensitivity that is adapted to the emission spectrum of the light source.

In a further advantageous refinement, it is provided that the light source emits light in the spectral region between 380 nm and 515 nm, and that the measurement fields have, in particular, a spectral sensitivity whose sensitivity maximum lies inside the wavelength region of 380 nm to 515 nm.

In a further advantageous refinement, it is provided that the measurement fields form a matrix, in particular a two-dimensional matrix, whose extent in each direction is greater than the light exit surface, in particular at least twice as large in each direction as the diameter or the relevant length of the light exit surface.

In a further advantageous refinement, it is provided that in a fashion bordering on the surface or matrix defined by the measurement fields the light measuring device has a stop that delimits the movement of the light guiding device at its light outlet in the direction of the stop.

In a further advantageous refinement, it is provided that the stop at least partially surrounds the measurement fields forming the measurement field arrangement, and overtops their surface.

In a further advantageous refinement, it is provided that the side lengths of the measurement field arrangement are greater than the diameter of the light exit surface and in an amount, in particular, of approximately 25 mm or less.

In a further advantageous refinement, it is provided that the measurement fields are designed as sensors of the light measuring device in the form of mutually identical photosensors that operate using the principle of coupled charge carriers (CCD) and extend two-dimensionally in the fashion of a matrix.

In a further advantageous refinement, it is provided that the light measuring device has a display device or is connected to a display device via which the illumination intensity measured by the light measuring device can be displayed in mW/cm$^2$ and/or the diameter of the light exit surface of the light guide can be displayed.

In a further advantageous refinement, it is provided that the light exit surface is displayed in symbolized fashion on the display device and, in particular, occupies a part of the display surface of the display device.

In a further advantageous refinement, it is provided that the intensity of the irradiation of the measurement fields by the light source is displayed on the display device by means of brightness differences and/or different colors.

In a further advantageous refinement, it is provided that the shape of the light source displayed on the display device corresponds to the light exit surface and has, in particular, a shape that is round, oval, angular or deviates from the circular shape.

In a further advantageous refinement, it is provided that the light measuring device has a storage device with the aid of which the result of at least one measurement operation can be stored, and/or via which the change in the light output of the light source can also be determined.

In a further advantageous refinement, it is provided that the light measuring device has at least one interface via which data can be exchanged with an external device, in particular via a wired or a wireless connection.

In a further advantageous refinement, it is provided that the light measuring device has an internal current source and/or an external current source, and in that, in particular, a rechargeable battery that is used in the light measuring device is compatible with the rechargeable battery used in the light curing device.

In a further advantageous refinement, it is provided that the light measuring device can be connected to a docking station, in particular to the docking station of a light curing device.

In a further advantageous refinement, it is provided that each measurement field emits an output signal whose magnitude corresponds to the illumination intensity of the measurement field which is produced by the light source.

In a further advantageous refinement, it is provided that each measurement field emits an output signal that corresponds either to the "illuminated" lighting state or the "non-illuminated" lighting state.

BRIEF DESCRIPTION OF THE FIGURES

Further advantages, details and features emerge from the following description of an exemplary embodiment of the invention with the aid of the drawings, in which.

DETAILED DESCRIPTION

Figure 1:
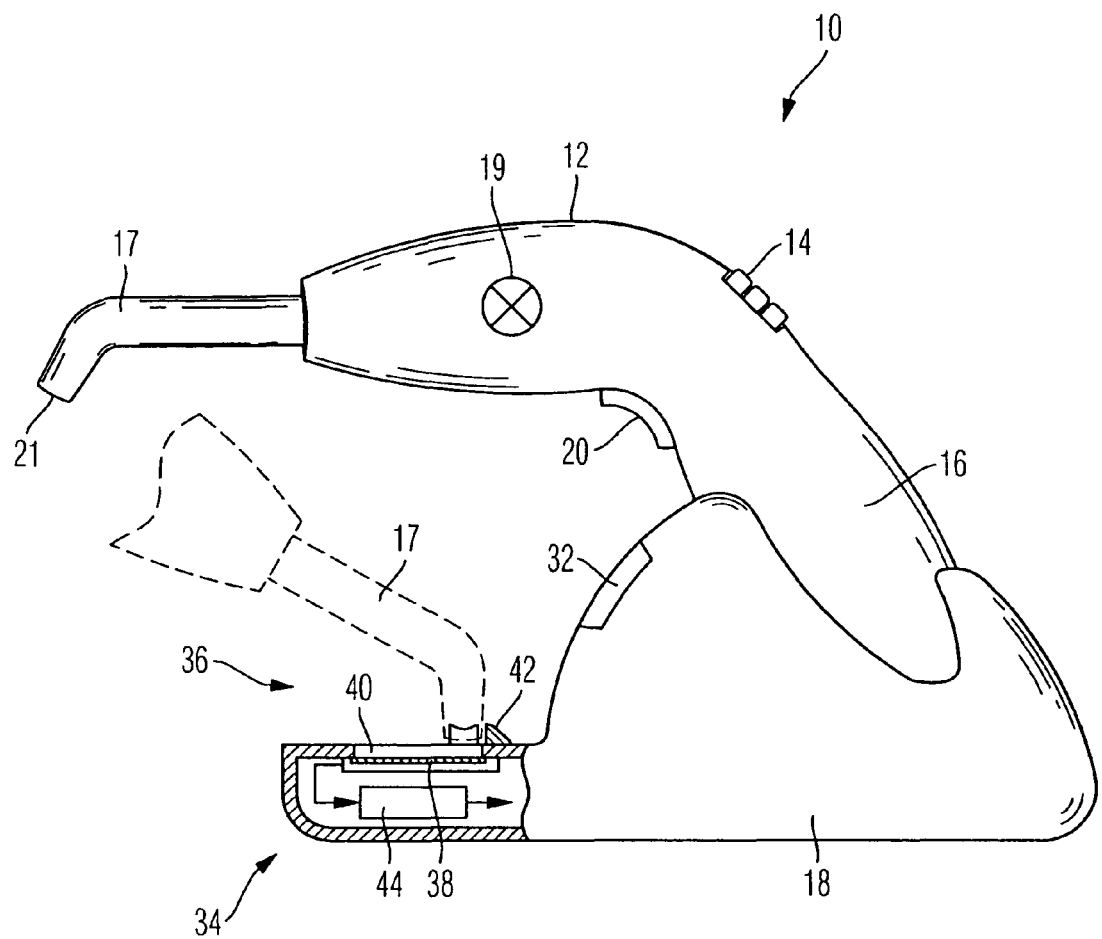
FIG. 1 shows a schematic arrangement of an inventive light measuring device in combination with a light curing device.

The light curing device 10 illustrated in FIG. 1 has a housing 12 and a display device 14 that is located on top of the rear side on a pistol grip 16 of the light curing device 10. At the front end of the housing 12, the light curing device has a light guiding device 17 that feeds light from a schematically illustrated light source 19 to a light exit surface 21 at the front end of the light guiding device.

As an exemplary device that accommodates a light source 19, the light curing device 10 can be put down in a base station 18. In a way known per se, the device has in the pistol grip storage batteries that, when the device is put down in the base station 18, are automatically charged whenever the charge state of the storage batteries so requires. The light curing device can be switched on via a momentary contact switch 20 that is arranged on the inner side of the pistol grip 16 in a way known per se. In the switched-on state of the device, light is emitted by the schematically indicated light source 19 and via the light guiding device 17.

The front end of the light guiding device is bent over in order to attain a simplified access to places that are hard to reach and where it is necessary to undertake light curing of material to be polymerized. The bending over results in an oblique position of the light exit surface 21 both in relation to the user's hand surrounding the pistol grip 16, and in relation to the principal axis of the light curing device 10, which runs through the light source 19 and the light guiding device 17.

The light exit surface 21 can, for example, have a transparent cover or else a positive lens.

The base station 18 is configured in a particular way in the illustrated exemplary embodiment. It comprises a light measuring device, indicated generally at 34, that is constructed at the front end of the base station 18, and a display device 32 that—if appropriate together with the display device 14—displays the charging state of the rechargeable batteries, and/or further parameters of the light curing device 10 on the latter.

The light measuring device 34, which can also be configured in a fashion separated spatially from the base station 18, serves the purpose of checking whether the optical properties of the light curing device 10—that is to say independently of the charging condition of the rechargeable batteries—are sufficient to ensure successful through curing of the dental restorative materials to be polymerized.

An adequate light emission is decidedly important, because in the event of insufficient light emission there is no complete polymerization of the dental restorative parts, and this is particularly critical for various reasons.

The light emission can worsen, for example, through worsening of the light source, soiling of the reflectors fitted there, scratching or clouding of positive lenses on the light guiding device 17, mechanical faults such as housing cracks or the like, or maloperation of the control device for the emission of light in the light curing device, it being impossible to derive a malfunction directly from the data of the display devices 14 and 32.

According to the invention, however, the light emission can be checked with the aid of the light measuring device 34. To this end, the light measuring device has a measurement field arrangement 36 that consists of a multiplicity of individual measurement fields 38 that are arranged next to one another in two dimensions, which measure the light emerging there and convert it into electrical signals.

The measurement field arrangement 36 is protected by a likewise two-dimensional window 40 that has, for example, a transparent cover such that the measurement fields 38 are protected against soiling.

Furthermore, the light measuring device 34 has a stop 42 that extends directly in bordering fashion up to the rear end of the measurement field arrangement 36 as a stop for the light guiding device 17. The light guiding device 17 is additionally illustrated in dashed form in order to make clear the position of the light curing device during calibration of and detecting the emitted light power. It is to be seen that the preferred alignment is provided in such a way that the light exit surface 21 extends parallel to the window 40.

It may be seen that the light exit surface 21 is substantially smaller than the measurement field arrangement 36 and the window 40. In the case of the exemplary embodiment illustrated, the area ratio is 1 to 10, for example. A multiplicity of measurement fields 38 therefore remain uncovered by the light exit surface 21 and are exposed to the incidence of daylight or artificial light from the surroundings of the base station 18.

In order to prevent corruption of the measurement result, provision is therefore made in one embodiment of a filter device that is tuned to the emitted wavelength of the light curing device 10 and reaches, for example, into the UV region and therefore renders it possible to make a distinction from ambient light. Alternatively, the detection of ambient light can also be defined as "unilluminated" such that illumination by the light exit surface 21 can be assumed only when light is received from the measurement fields above a prescribed threshold.

In order to avoid the impingement of spurious light from the surroundings on the free regions 46 of the measurement field arrangement 36, it is also possible to provide an annular sealing lip, for example made from rubber, above the window 40 that is then penetrated by the light guiding device or the shank of the light curing device 10, the sealing lip being sealed against the light curing device 10.

The output signal of all the measurement fields 38 is detected and fed to an evaluation circuit 44. The evaluation circuit 44 detects both the intensity of the emitted radiation of the individual measurement fields, and for which measurement field 38 there is no illumination or an illumination with ambient light. The measurement values detected here are used to integrate the entire illumination intensity, the illumination with ambient light being defined, if appropriate, as "unilluminated".

On the basis of the measurement result thus recorded, it is possible—given that the matrix or arrangement of the measurement fields 38 is provided in two-dimensional fashion—to determine both the diameter of the light exit surface 21 and the shape thereof, and also the illumination intensity emitted by the light source, it also then being possible to display said intensity on the display device 32.

Figure 2:
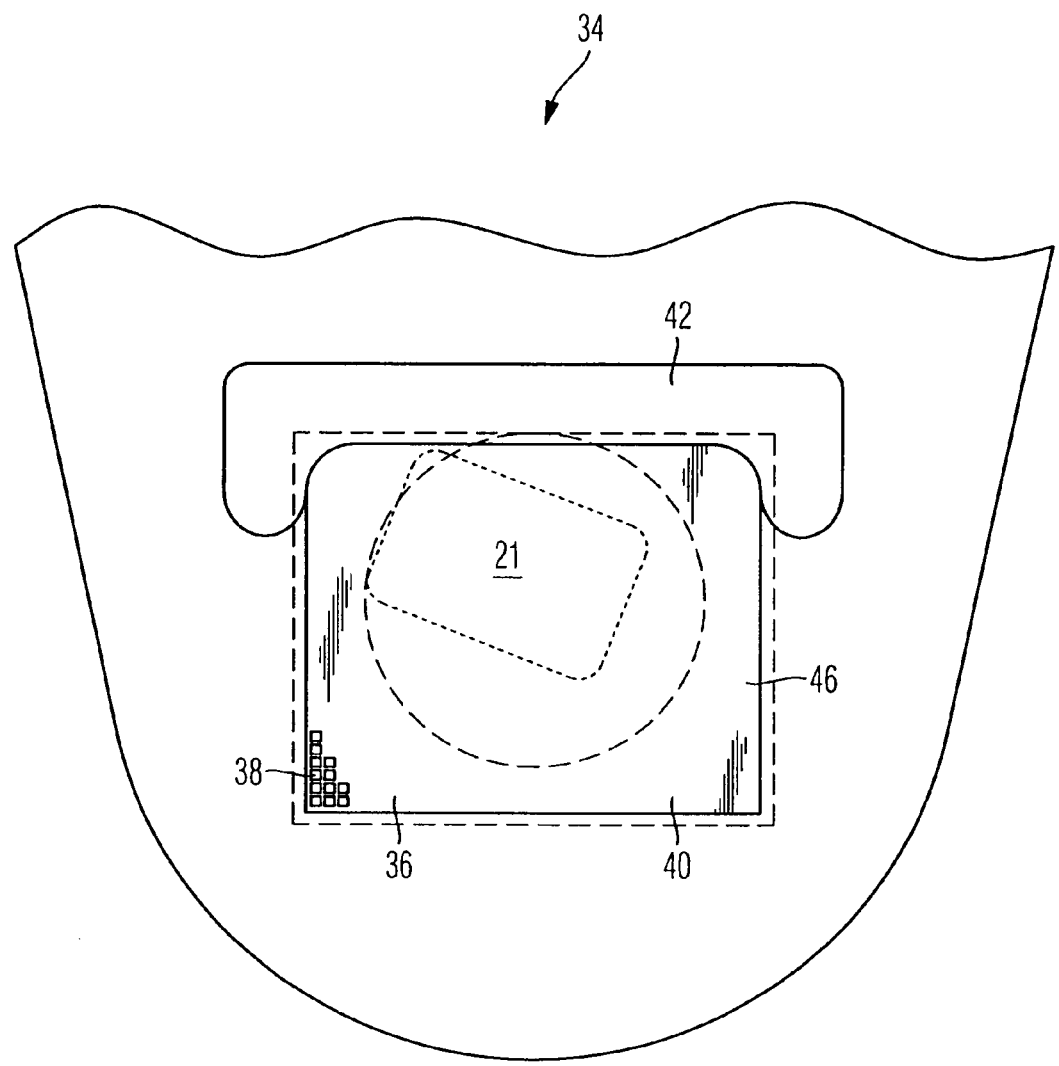
FIG. 2 shows a schematic view of an inventive light measuring device in plan view.

A light measuring device 34 in an enlarged illustration is to be seen in FIG. 2. The stop 42 is essentially formed in a U-shaped fashion and laterally borders the window 40, which covers the measurement field arrangement 36.

Individual measurement fields 38 are illustrated here schematically, it being understood that corresponding measurement fields 38 are distributed uniformly over the entire measurement field arrangement 36.

The light exit surface 21 of the light curing device 10 can be placed reliably in the detection region of the measurement field arrangement 36 by the implementation of the stop 42. As is indicated by the various light exit surfaces 21 illustrated by dashes and dots in FIG. 2, the exact arrangement is not decisive here.

In a modified arrangement, the stop 42 surrounds the window 40 such that the light exit surface 21 always remains above the window 40.

As may be seen from FIG. 2, an oblique and a light exit surface is also detected straight away that deviates in shape from a round one.

According to the invention, it is consequently possible to record exactly with marked precision the size of the light exit surface and also the illumination intensity.

It goes without saying that the light measuring device 34 can also be fitted independently of the base station 18, and it is also possible to implement a central light measuring device for a multiplicity of light curing devices 10. In this case, it is also sensible to code the relevant light curing device or its handpiece such that the light measuring device 34 can detect which particular handpiece can be measured. In the case of this refinement, the measured values are preferably detected and stored, and it is determined from a worsening of the optical properties when it is to be expected that the light curing device will require a general overhaul.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A light measuring device, in combination with a dental light curing device (10) having a light source (19) and a light guiding device (17) terminating in light exit surface, the light measuring device (34) comprising:
> at least four measurement fields (38) arranged next to one another in two dimensions, wherein the light measuring device (34) can detect the total illumination intensity of light that exits from a light exit surface (21) of the light guiding device (17) of the light curing device (10), the measurement fields (38) forming a two-dimensional matrix whose extent in each direction is greater than the light exit surface (21), and whereby the illumination intensity is detected by integrating output signals of the measurement fields.

2. The light measuring device as claimed in claim 1, wherein the measurement fields (38) extend in two mutually perpendicular dimensions in a prescribed grid size and have a spectral sensitivity that is adapted to the emission spectrum of the light source (19).

3. The light measuring device as claimed in claim 1, wherein the light source (19) emits light in the spectral region between 380 nm and 515 nm, and wherein the measurement fields (38) have a spectral sensitivity whose sensitivity maximum lies inside the wavelength region of 380 nm to 515 nm.

4. The light measuring device as claimed in claim 1, wherein the measurement fields (38) are at least twice as large in each direction as the diameter of the light exit surface (21).

5. The light measuring device as claimed in claim 1, wherein the light measuring device (34) has a stop (42) that limits the movement of the light guiding device (17) at its light outlet in the direction of the stop (42).

6. The light measuring device as claimed in claim 5, wherein the stop (42) at least partially surrounds the measurement fields (38) forming the measurement field arrangement (36), and extends above the surface of the measurement field arrangement (36).

7. The light measuring device as claimed in claim 1, wherein the measurement fields (38) extend in two mutually perpendicular dimensions in a prescribed grid size, and wherein the side lengths of the measurement field arrangement (36) are greater than the diameter of the light exit surface (21) and in an amount of approximately 25 mm or less.

8. The light measuring device as claimed in claim 1, wherein the measurement fields are designed as sensors of the light measuring device (34) in the form of mutually identical photosensors that operate using the principle of coupled charge carriers (CCD).

9. The light measuring device as claimed in claim 1, wherein the light measuring device (34) is connected to a display device (14) via which the diameter of the light exit surface of the light guide can be displayed.

10. The light measuring device as claimed in claim 9, wherein the light exit surface (21) is displayed in symbolized fashion on the display device (14) and occupies a part of the display surface of the display device (14).

11. The light measuring device as claimed in claim 9, wherein the shape of the light source (19) displayed on the display device (14) corresponds to the light exit surface (21).

12. The light measuring device as claimed in claim 1, wherein the light measuring device (34) is connected to a display device (14) via which the illumination intensity measured by the light measuring device (34) can be displayed in on the display device (14) by means of brightness differences and/or different colors.

13. The light measuring device as claimed in claim 1, wherein the light measuring device (34) has a storage device with the aid of which the result of at least one measurement operation can be stored, and via which the change in the light output of the light source (19) can also be determined.

14. The light measuring device as claimed in claim 1, wherein the light measuring device (34) has at least one interface via which data can be exchanged with an external device via a wired or a wireless connection.

15. The light measuring device as claimed in claim 1, wherein the light measuring device (34) has a rechargeable battery that is used in the light measuring device (34) and which is compatible with a rechargeable battery used in the light curing device (10).

16. The light measuring device as claimed in claim 1, wherein the light measuring device (34) can be mounted on a docking station of a light curing device (10).

17. The light measuring device as claimed in claim 1, wherein each measurement field (38) emits an output signal whose magnitude corresponds to the illumination intensity of the measurement field (38) which is produced by the light source (19).

18. The light measuring device as claimed in one of claims 1, wherein each measurement field (38) emits an output signal that corresponds either to the illuminated lighting state or the nonilluminated lighting state.

19. The light measuring device as claimed in claim 1, wherein the light measuring device (34) is connected to a display device (14) via which the illumination intensity measured by the light measuring device (34) can be displayed in mW/cm$^2$.

20. A light measuring device, in combination with a dental light curing device (10) having a light source (19) and a light guiding device (17) terminating in light exit surface, the light measuring device (34) comprising:
> at least four measurement fields (38) arranged next to one another in two dimensions, wherein the light measuring device (34) can detect the total illumination intensity of light that exits from a light exit surface (21) of the light guiding device (17) of the light curing device (10), the measurement fields (38) forming a two-dimensional matrix whose extent in each direction is greater than the light exit surface (21), whereby the illumination intensity is detected by integrating output signals of the measurement fields, and whereby obliquity errors detected, can be compensated.

21. The light measuring device of claim 20, wherein the obliquity errors are compensated by a control device that undertakes a correction with a correction table when different illumination intensities of the measurement fields that correspond to a gradient indicate the obliquity of the light curing device.

* * * * *